United States Patent [19]

Halm et al.

[11] Patent Number: 5,738,685
[45] Date of Patent: Apr. 14, 1998

[54] OSTEOSYNTHESIS DEVICE

[75] Inventors: Henry Halm, Bissendorf-Wissingen; Günther Rehder, Winterbach; Bernd Schäfer, Schorndorf, all of Germany

[73] Assignee: Schafer micomed GmbH, Schorndorf, Germany

[21] Appl. No.: 545,576
[22] PCT Filed: Apr. 8, 1994
[86] PCT No.: PCT/EP94/01095
 § 371 Date: Jan. 29, 1996
 § 102(e) Date: Jan. 29, 1996
[87] PCT Pub. No.: WO94/26191
 PCT Pub. Date: Nov. 24, 1994

[30] Foreign Application Priority Data

May 18, 1993 [DE] Germany ............ 43 16 542.7

[51] Int. Cl.⁶ ...................................... A61B 17/56
[52] U.S. Cl. ............... 606/61; 606/73; 606/72; 411/308; 411/426
[58] Field of Search ............... 606/61, 60, 73, 606/72; 411/429, 433, 430, 432, 427, 308, 426

[56] References Cited

U.S. PATENT DOCUMENTS

| | | | |
|---|---|---|---|
| 5,176,680 | 1/1993 | Vignaud et al. | 606/61 |
| 5,226,766 | 7/1993 | Lasner | 606/73 |
| 5,261,912 | 11/1993 | Frigg | 606/72 |
| 5,306,275 | 4/1994 | Bryan | 606/73 |
| 5,443,467 | 8/1995 | Biedermann et al. | 606/73 |
| 5,496,321 | 3/1996 | Duno et al. | 606/61 |
| 5,499,983 | 3/1996 | Hughes | 606/73 |
| 5,562,663 | 10/1996 | Wisnewski et al. | 606/73 |

FOREIGN PATENT DOCUMENTS

| | | |
|---|---|---|
| 0077681B1 | 11/1986 | European Pat. Off. . |
| 0 346 521 A1 | 12/1989 | European Pat. Off. . |
| 0 348 272 A1 | 12/1989 | European Pat. Off. . |
| 0 384 001 A | 8/1990 | European Pat. Off. . |
| 0 443 892 A1 | 8/1991 | European Pat. Off. . |
| 0 443 894 A1 | 8/1991 | European Pat. Off. . |
| 0 465 158 A2 | 1/1992 | European Pat. Off. . |
| 0 528 706 A1 | 2/1993 | European Pat. Off. . |
| 3722590 | 12/1988 | France ............ 606/61 |
| 2 624 720 | 6/1989 | France . |
| 39 42 429 A1 | 8/1990 | Germany . |
| 39 16 198 A1 | 11/1990 | Germany . |
| 91 04 027 U | 8/1991 | Germany . |
| 9104027 U | 8/1991 | Germany . |
| 90 04 240 U | 9/1991 | Germany . |
| 4012506A1 | 10/1991 | Germany . |
| 9011312 U | 1/1992 | Germany . |
| 41 10 002 C1 | 5/1992 | Germany . |
| 41 07 480 A1 | 9/1992 | Germany . |
| 2 178 323 | 2/1987 | United Kingdom . |

Primary Examiner—Michael Buiz
Assistant Examiner—Julian W. Woo
Attorney, Agent, or Firm—Jones, Tullar & Cooper, P.C.

[57] ABSTRACT

An osteosynthesis device having a bone screw, particularly a pedicle screw, a fork head that has a groove and a corrective pin seated in the groove of the fork head. A corrective pin is secured against twisting in that the bottom of the groove of the fork head is provided with a plurality of longitudinal slots lying parallel to one another.

21 Claims, 2 Drawing Sheets

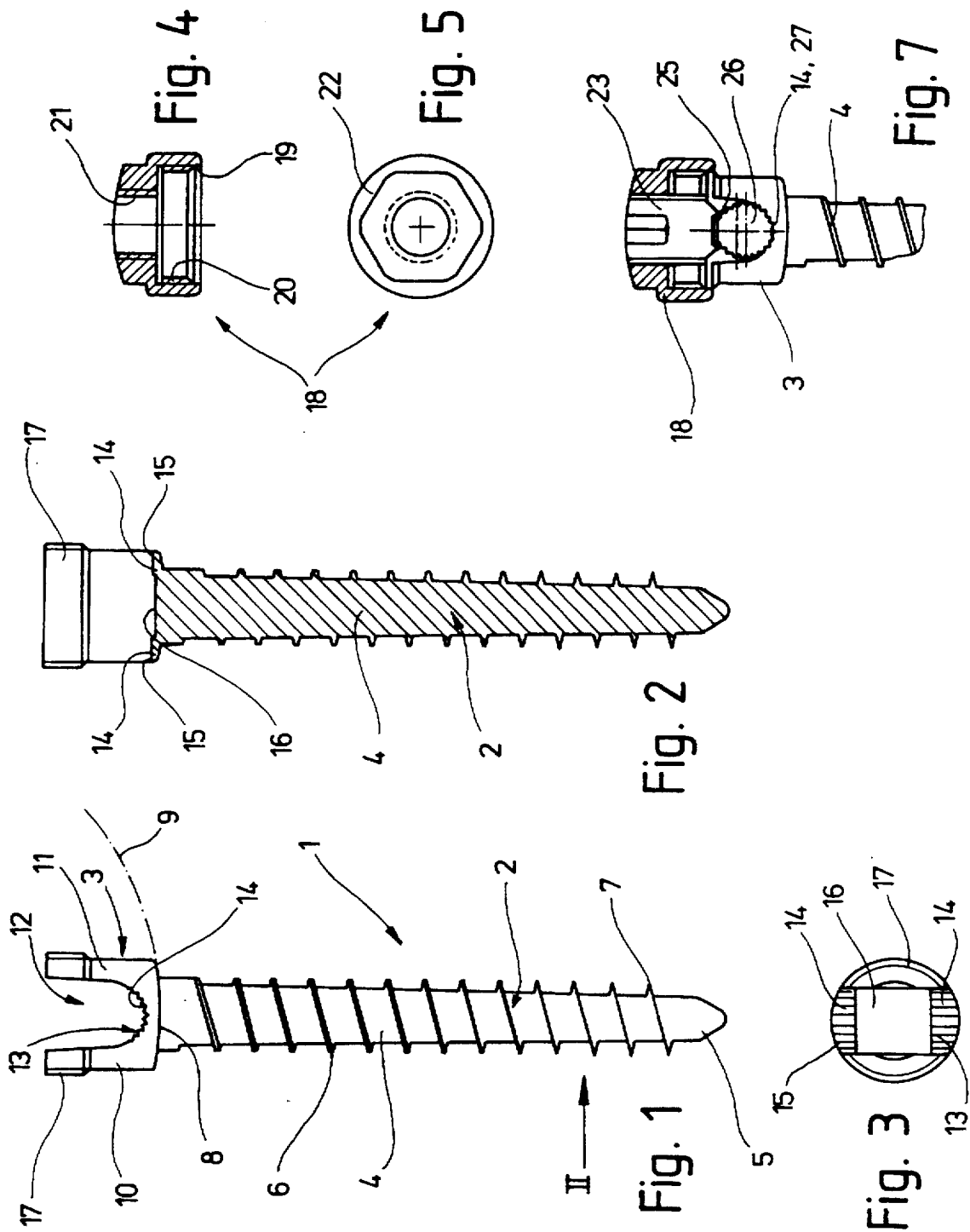

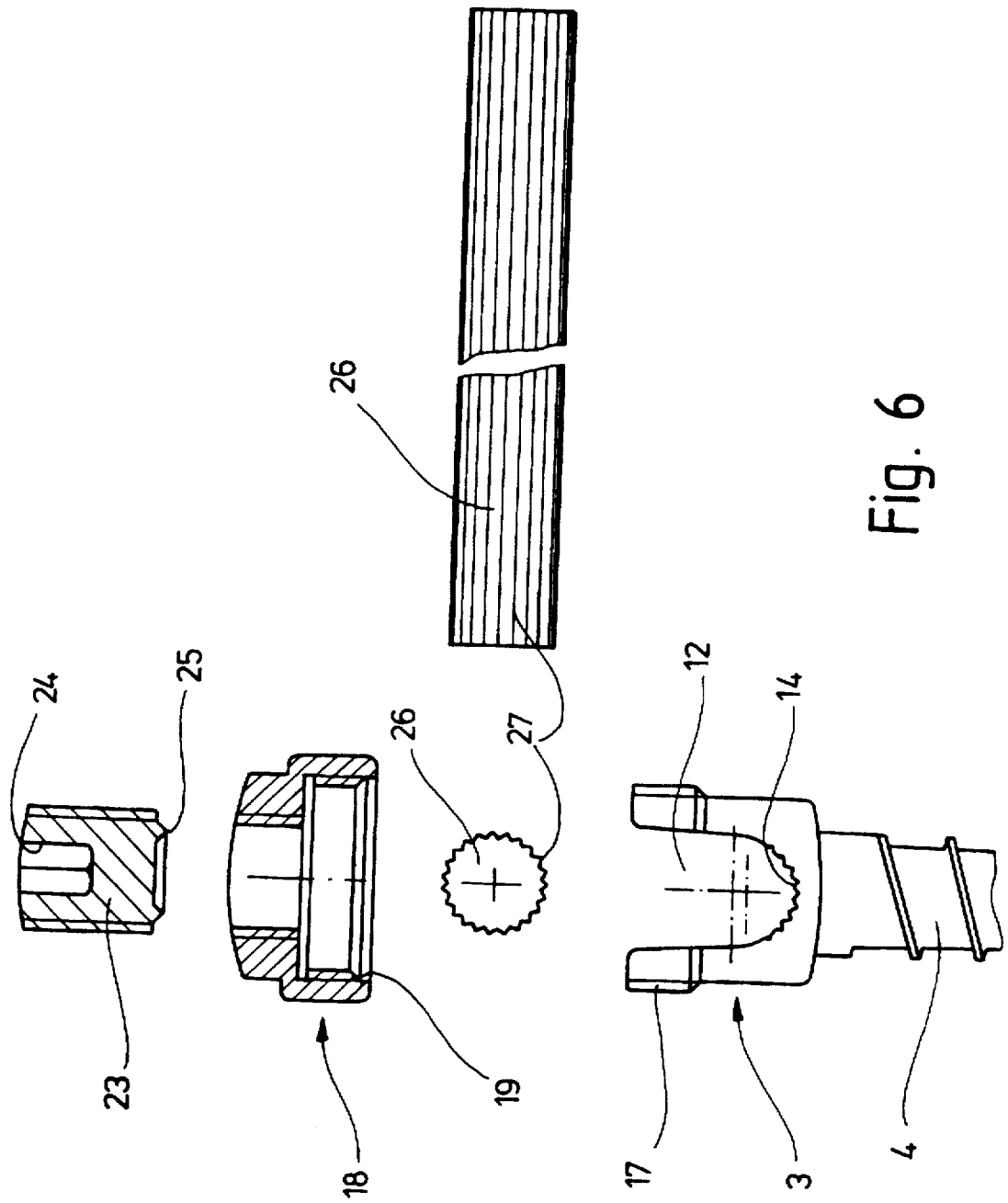

OSTEOSYNTHESIS DEVICE

FIELD OF THE INVENTION

The present invention relates to an osteosynthesis device having a bone screw, particularly a pedicle screw, a fork head that has a groove and a corrective pin seated in the groove of the fork head.

BACKGROUND OF THE INVENTION

A large number of osteosynthesis devices of this type are known, for example from German Utility Model DE-Gbm 91 04 027, European Patent Application EP-A-346 521, German Patent Application DE-A 39 42 429, European Patent Application EP-A-443 894, European Patent Application EP-A-348 272, European Patent Application EP-A-465 158, European Patent Application EP-A-528 706, European Patent Application EP-A-443 892, German Patent Application DE-A 39 16 198, and German Patent Publication DE-C 41 10 002. Various bone screws with forked heads are known from these references into which a corrective pin can be inserted and fixated. This primarily involves a non-slip bracing against the bone screw. Only a slip-free and twist-free fixation of the corrective pin against the bone screw assures an optimum transfer of pulling and pressing forces onto the individual bones to be corrected and fixated, as well as the transfer of torque and bending moments.

As a rule, a good fixation is achieved in that a fastening screw is screwed into the fork head in such a way that the screw presses on the inserted corrective pin. It has been shown, however, that an upward bending of the fork head is not to be ruled out because of the high forces and moments occurring, so that the fastening of the corrective pin can loosen. Moreover, a clamping fixation of this type does not offer adequate insurance against twisting of the corrective pin around its own axis.

With a clamping osteosynthesis implant (European Patent Application EP-A-528 706), a fixing plate is placed onto the corrective pin inserted into the fork head of the bone screw; the task of this plate on the one hand is to prevent the two legs of the fork head from being pressed apart and, on the other hand, it has longitudinal grooves on its section resting on the corrective pin that engage longitudinal grooves of the corrective pin. By means of this, an increased insurance against twisting of the corrective pin in the fork head is achieved; however, the total torque acting on the corrective pin must be transferred onto the bone screw via the pressing plate, a fastening screw and the two legs of the fork head. At high torques, there is still the danger that the fork head will become deformed and, because of this, the fixation of the corrective pin will be loosened.

OBJECT AND SUMMARY OF THE INVENTION

Therefore an object of present invention is to further develop an osteosynthesis device of the type mentioned at the outset in such a way that the corrective pin can be placed against the bone screw in a manner that is fixed against twisting.

This object is attained in accordance with the present invention in that the bottom of the groove of the fork head is provided with a plurality of longitudinal slots lying parallel to one another.

The longitudinal slots provided at the bottom of the groove of the fork head, that is, at the bottom of the groove into which the corrective pin is inserted, permit, on the one hand, a fixation secure against twisting of the corrective pin against the bone screw and, on the other hand, a direct transfer of force from the corrective pin onto the shaft of the bone screw. When a corrective pin with a smooth surface is placed into the fork head, the longitudinal slots dig into the surface of the corrective pin and fixate it in this manner. If the corrective pin is embodied as a threaded rod, then the longitudinal slots dig into the thread of the threaded rod. In an advantageous manner, the longitudinal slots extend in the direction of the axis of the corrective pin. In other embodiments the longitudinal slots can also extend diagonally or transversely.

The embodiment of the bone screw in accordance with the present invention has the advantage that the transfer of force from the corrective pin onto the shaft of the bone screw is not effected via holding elements, screws or the two legs of the fork head, but directly from the pin onto the shaft. In this way significantly higher forces and moments can be transferred, or the force or the moment can be transferred with greater insurance against slipping or slipping through.

In an advantageous manner, the corrective pin is provided with longitudinal grooves, wherein the longitudinal grooves correspond to the longitudinal slots and, in particular, extend in the direction of the axis. In this embodiment the longitudinal grooves engage the longitudinal slots of the fork head when the corrective pin is inserted into the groove of the fork head, and produce a positive lockup connection between the corrective pin and the bone screw. In this instance, both the corrective pin and the fork head can be made of a hard, deformation-resistant material. Hard or tough material is particularly recommendable for the transfer of high forces and moments.

Problem-free insertion of the corrective pin into the groove of the fork head and subsequent removal is achieved in that the longitudinal slots are embodied without an undercut in the direction of the axis of the bone screw. Because the longitudinal slots do not have undercuts, the corrective pin can be removed from the groove again without problems after a deformation during pressing into the longitudinal slots without becoming caught in the longitudinal slots.

The longitudinal slots are preferably provided at the edge of the fork head. This has the advantage that, because of the shorter longitudinal slots, substantially higher pressing forces can be attained during pressing of the corrective pin, so that the longitudinal slots can dig significantly better into the surface of the corrective pin if it is smooth. Moreover, by means of the higher pressure, the holding force is increased with both smooth and grooved corrective pins.

The fork head of the bone screw is preferably provided with an outside thread, particularly for a head nut. This head nut, which is screwed onto the corrective pin after the latter has been inserted into the fork head, prevents the two legs of the fork head from bending apart under a high force effect. Moreover, by means of the head nut the corrective pin can be pressed into the bottom of the fork head.

It is provided in a further development that the head nut has an inside thread with a centering collar. This centering collar significantly facilitates the placement of the head nut onto the fork nut, so that problem-free, fast screwing on of the head nut is also possible in difficult-to-access positions, such as those that occur continually during surgical operations, for example with ventral seating of the corrective pin.

In an exemplary embodiment the head nut is embodied as a cap nut and has a coaxial inside thread for a fastening screw. In this exemplary embodiment the corrective pin is pressed into the bottom of the fork head via the fastening screw.

In a further development it is provided that the fastening screw has a cup point at the screwed-in end, and is particularly embodied as a hexagon socket screw. When the fastening screw is tightened, the screwed-in end digs via the cup point into the area of the corrective pin located in the fork head, and the end additionally holds it against slipping or twisting.

In an advantageous manner the axial front surface of the head nut, that is, the top side of the head nut, is embodied to be ball-shaped, particularly spherical, and in particular is encircled by a hexagon. Via the hexagon, the head nut can be screwed onto the fork head of the bone screw and tightened in a simple manner. The spherical shape has the advantage that the adjacent tissue experiences less irritation.

In a preferred exemplary embodiment, the bone screw has a screw body that extends conically from the point of the screw in the direction of the fork head. The conical shape of the screw body has the advantage that the bone screw can be better fixated in the bone, and in particular sits tightly in the bones when screwed in. The bone screw is not held only via the threads, but also by means of the clamping effect of the conically expanding screw body.

The outer or nominal diameter of the bone screw, i.e., the thread diameter, is preferably constant. In this case, in an advantageous manner the width of the thread of the bone screw increases starting from the point of the screw. Because of this, a clamping effect is also obtained, by means of which the bone screw is additionally held against the bone. In the process, the thread pitch preferably remains constant.

In an advantageous manner, the end of the fork head connected to the screw body is embodied to be ball-shaped, particularly spherical. By means of the ball- or spherical shape, the advantage is attained that, even with an oblique or inclined arrangement of the bone screw on a bone plate, particularly in the distal region, it nevertheless rests fully in the receiving cap of the bone plate.

Further advantages, features and details of the present invention ensue from the following description, in which a particularly preferred exemplary embodiment is represented in detail with reference to the drawings. With the present invention, features shown in the drawings and mentioned in the description can be realized either individually in and of themselves, or in arbitrary combinations.

BRIEF DESCRIPTION OF THE DRAWINGS

FIG. 1 is a side view of the bone screw in accordance with the present invention;

FIG. 2 is a side view in the direction of the arrow II of FIG. 1, partly in section;

FIG. 3 is a top view of the bone screw;

FIG. 4 is a longitudinal section through a head nut;

FIG. 5 is a top view of the head nut;

FIG. 6 is an exploded representation of the upper part of the bone screw with the corrective pin to be inserted, head nut and fastening screw; and FIG. 7 is an assembly representation of the elements of FIG. 6.

DETAILED DESCRIPTION OF THE PREFERRED EMBODIMENT

FIG. 1 shows a bone screw, particularly a pedicle screw, indicated in its entirety by 1, that has a threaded shaft 2 and a fork head 3. The threaded shaft 2 comprises a screw body 4 with a screw point 5 and a thread 6 on the outside of the screw body 4. It can be seen here that the screw body 4 extends conically from the screw point in the direction of the fork head 3. The diameter of the thread 6 remains constant, whereas the width of the thread 7 increases in the direction of the fork head 3, starting from the screw point 5. However, the pitch of the thread 6 remains constant across the entire length of the thread shaft 2. Moreover, it can be seen in FIG. 1 that the underside 8 of the fork head 3 is embodied to be ball-shaped, particularly spherical, which is intended to be indicated by the line 9.

The fork head 3 has two legs 10 and 11, between which a groove 12 is defined. The groove 12 has slightly conically-opening groove walls. The bottom 13 of the groove 12 is provided with longitudinal slots 14, as can also be seen in FIG. 3. Further, it can be seen that the longitudinal slots 14 are cut without undercuts into the bottom 13 of the groove 12. As can be seen in FIGS. 1 through 3, the longitudinal slots 14 are located at the edge 15 of the groove 12, whereas the central region of the groove collar is free from longitudinal slots. The longitudinal slots 14 are formed either by means of milling or stamping.

The upper end of the fork head 3 is provided with an outside thread 17, which extends across approximately one-third of the height of the fork head 3. A head nut 18 (FIG. 4) embodied as a cap nut can be screwed onto this outer thread 17. At its lower end, the head nut 18 has a centering collar 19, which is followed by an inside thread 20 (first inside thread). Coaxial to the inside thread 20, the head nut 18 is provided with a further inside thread 21 (second inside thread) that has a smaller nominal diameter. The top side of the head nut 18 is likewise embodied to be ball-shaped or spherical. As can be seen from FIG. 5, the top side of the head nut 18 has a hexagonal outside 22, by means of which the head nut 18 can be screwed on the bone screw 1 and secured.

A fastening screw 23 (FIG. 6) can be screwed into the inside thread 21. The fastening screw 23 is likewise embodied on its top side to be ball-shaped, and has a hexagon socket 24. On the underside, the fastening screw 23 is provided with a cup point 25 that presses onto a corrective pin 26 when the fastening screw 23 is tightened. This corrective pin 26 (FIG. 6) is provided with longitudinal grooves 27, which correspond to the longitudinal slots 14 of the bottom 13 of the groove 12.

When the corrective pin 26 is inserted into the groove 12 of the fork head 3, as shown in FIG. 6, the longitudinal grooves 27 engage the longitudinal slots 14 with positive lockup. Subsequently the head nut 18 is screwed on, and the centering collar 19 significantly facilitates a placement of the head nut 18 on the outside thread 17. Finally, the fastening screw 23 is screwed in and secured, wherein the cup point 25 digs into the adjacent longitudinal grooves 27. In this way, the corrective pin 26 is fixed against twisting by the longitudinal grooves 27 that engage the longitudinal slots 14, and against displacement via the cup point 25 dug into the longitudinal grooves 27. Moreover, torque is transmitted by the corrective pin 26, via the positive lockup connection with the longitudinal slots 14, directly into the screw body 4 (FIG. 7).

We claim:

1. An osteosynthesis device, comprising:
   a bone screw; and
   a corrective pin having an outer surface provided with longitudinal grooves, wherein:
   said bone screw includes a fork head defining a groove at the bottom of which a plurality of parallel, longitudinal slots are provided, and an outside thread for receiving a head nut with an inner thread for engaging said outside thread; and said corrective pin being seated in said groove of said fork head for engagement of said grooves of said corrective pin with said slots.

2. The osteosynthesis device as defined in claim 1, wherein said bone screw is embodied as a pedicle screw.

3. The osteosynthesis device as defined in claim 1, wherein the longitudinal extent of said slots is in the direction of the axis defined by said corrective pin.

4. The osteosynthesis device as defined in claim 1, wherein said longitudinal slots are embodied without undercuts in the direction of the axis defined by said bone screw.

5. The osteosynthesis device as defined in claim 1, wherein said groove defines an edge, and wherein said longitudinal slots are provided at said edge.

6. The osteosynthesis device as defined in claim 1, wherein said longitudinal grooves correspond to said longitudinal slots.

7. The osteosynthesis device as defined in claim 1, further comprising:

a head nut defining an inner thread and a centering collar.

8. The osteosynthesis device as defined in claim 7, wherein said head nut is embodied as a cap nut defining a further inner thread which is coaxial with said inner thread.

9. The osteosynthesis device as defined in claim 8, further comprising:

a fastening screw, defining a cup point, said fastening screw engaging said further inner thread.

10. The osteosynthesis device as defined in claim 9, wherein said fastening screw is embodied as a hexagonal socket screw.

11. The osteosynthesis device as defined in claim 8, wherein said head nut defines an axial face end which is ball-shaped.

12. The osteosynthesis device as defined in claim 11, wherein said axial face end is hexagonal.

13. The osteosynthesis device as defined in claim 1, wherein said bone screw includes a body which defines a screw point at one end and said fork head at its other end, and wherein said body extends conically from said screw point to said fork head.

14. The osteosynthesis device as defined in claim 13, wherein the outside diameter of said bone screw is constant.

15. The osteosynthesis device as defined in claim 14, wherein said screw body widens to the diameter of said bone screw.

16. The osteosynthesis device as defined in claim 13, wherein said bone screw defines a thread which increases from said screw point to said fork head.

17. The osteosynthesis device as defined in claim 16, wherein the pitch of said thread is constant.

18. The osteosynthesis device as defined in claim 1, wherein said fork head defines an axial end face which is ball-shaped.

19. The osteosynthesis device as defined in claim 18, wherein said ball-shape in spherical.

20. A bone screw having:

a screw body defining a screw point at one end, and a fork head at the other end, said fork head having an outside thread for receiving a head nut, said screw body extending conically from said screw point in the direction of said fork head; and a thread formed on said screw body which extends from said screw point to said fork head, with the diameter of said thread being constant and the width of said thread increasing from said screw point to said fork head.

21. The bone screw as defined in claim 20, wherein the pitch of said thread formed on said screw body is constant.

* * * * *